United States Patent [19]

Mitsumaki et al.

[11] Patent Number: 5,104,807
[45] Date of Patent: Apr. 14, 1992

[54] ANALYZING APPARATUS IN WHICH LIQUID CAN BE STIRRED AND ANALYZING METHOD THEREOF

[75] Inventors: Hiroshi Mitsumaki, Mito; Fujiya Takahata, Katsuta, both of Japan

[73] Assignee: Hitachi, Ltd., Tokyo, Japan

[21] Appl. No.: 311,272

[22] Filed: Feb. 16, 1989

[30] Foreign Application Priority Data

Feb. 19, 1988 [JP] Japan .................. 63-35289

[51] Int. Cl.⁵ .................................. G01N 35/04
[52] U.S. Cl. ................................... 436/47; 366/218; 422/63; 422/64; 422/65; 422/67; 494/19
[58] Field of Search ............ 422/63, 64, 65, 67, 422/72, 102; 436/45, 47; 366/208, 218, 219, 287, 288; 494/19

[56] References Cited

U.S. PATENT DOCUMENTS

| | | | |
|---|---|---|---|
| 3,190,731 | 6/1965 | Weiskopf | 422/102 |
| 3,199,775 | 8/1965 | Drucker | 494/19 |
| 3,722,790 | 3/1973 | Natelson | 422/101 |
| 3,826,622 | 7/1974 | Natelson | 422/102 |
| 3,882,716 | 5/1975 | Beiman | 494/19 |
| 4,313,735 | 2/1982 | Yamashita et al. | |
| 4,479,220 | 10/1984 | Mochida et al. | 494/19 |
| 4,518,264 | 5/1985 | Nohso | 366/208 |
| 4,665,035 | 5/1987 | Tunac | 422/102 |
| 4,776,832 | 10/1988 | Martin et al. | 494/19 |
| 4,865,810 | 9/1989 | Simon | 494/19 |

FOREIGN PATENT DOCUMENTS

| | | |
|---|---|---|
| 2713678 | 10/1978 | Fed. Rep. of Germany . |
| 55-116262 | 9/1980 | Japan . |
| 57-42325 | 3/1982 | Japan . |
| 57-171266 | 10/1982 | Japan . |
| 2081118 | 2/1982 | United Kingdom . |

*Primary Examiner*—Peter Kratz
*Attorney, Agent, or Firm*—Fay, Sharpe, Beall, Fagan, Minnich & McKee

[57] ABSTRACT

An analyzing apparatus includes a turntable, and a plurality of reaction containers which are arranged on the turntable. This turntable is intermittently rotated so that the train of reaction containers is alternately in a conveyed state and a stopped state. The outer walls of part of the reaction containers in the train of reaction containers are in contact with a fixedly provided friction flange, while the remaining reaction containers in the train of reaction containers is not in contact with the friction flange. Since the reaction containers located in an area where they make contact with the friction flange are conveyed while they are contacting with the friction flange as the turntable is rotated, the motion of the turntable is transmitted to the reaction containers, and the reaction containers are thereby rotated on their own axes so as to allow the reaction liquid in the containers to be stirred. The rotation of the reaction containers on their own axes is stopped when they reach an area where they do not make contact with the friction flange. After the rotation of the reaction liquid in the reaction containers has been substantially stopped, the light measurement of the reaction liquid is performed using a photometer.

24 Claims, 3 Drawing Sheets

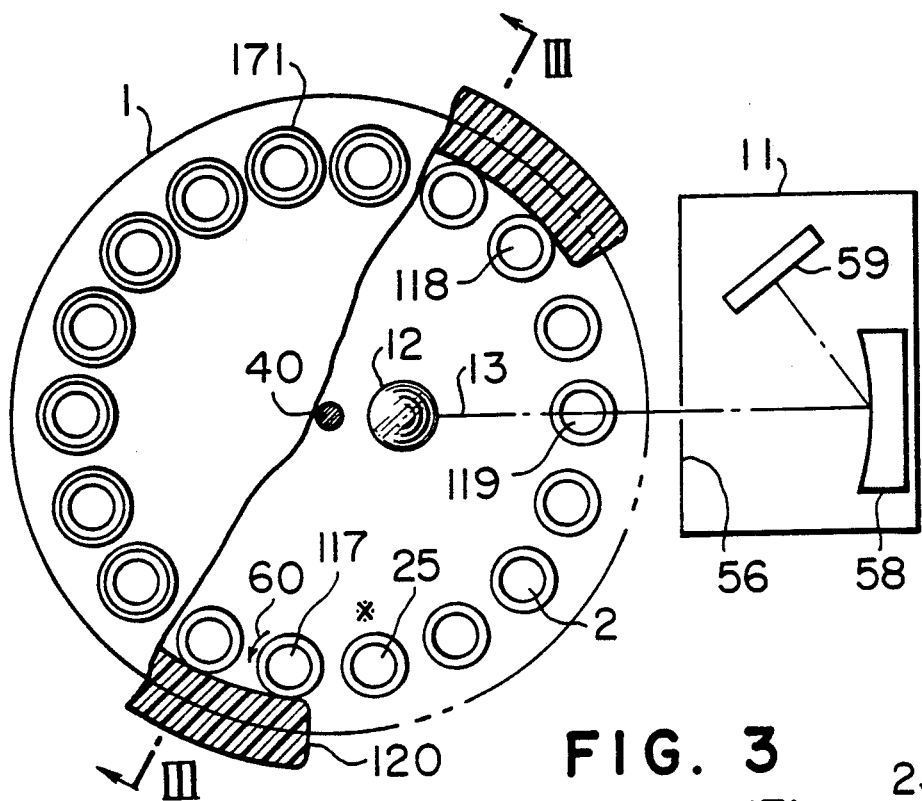
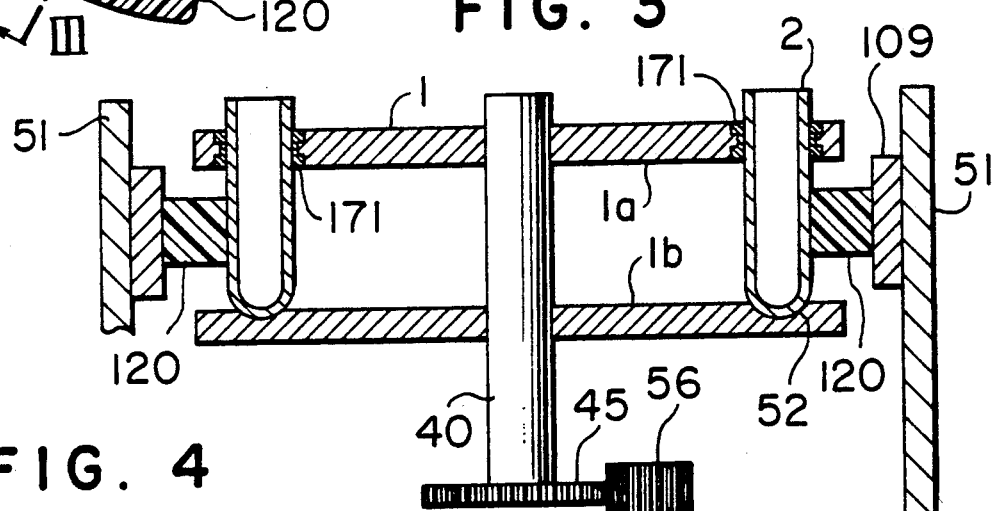
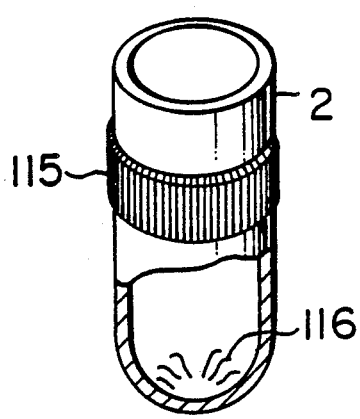

ANALYZING APPARATUS IN WHICH LIQUID CAN BE STIRRED AND ANALYZING METHOD THEREOF

BACKGROUND OF THE INVENTION

1. Field of the Invention

The present invention relates to an analyzing apparatus for measuring liquid samples and an analyzing method thereof. In particular, the present invention pertains to an analyzing apparatus which enables liquid samples accommodated in containers to be stirred by moving the containers, and an analyzing method thereof.

2. Description of the Related Art

When the trace components of a body fluid sample are measured utilizing the immune reaction, the possibility of the mutual contamination (carry over) of specimens must be reduced as much as possible. Also, in order to sequentially and stably cause the immunoreaction in a reaction container which contains a liquid sample and a reagent, it is necessary for the mixture solution of the liquid sample and the reagent to be stirred. Generally, the liquid contained in the reaction container is stirred by a stirring rod inserted into the reaction container. However, in this method, the possibility of the mutual contamination of the specimens is high.

Accordingly, some attempts have been made to stir the liquid contained in the reaction container without use of a stirring rod. For example, Japanese Patent Laid-Open No. 57-42325 (which corresponds to British Patent No. 2081118) discloses a stirring method in which a total of a large number of reaction containers arranged on a turntable are simultaneously rotated by rotating an annular rotary disk provided inside of the train of reaction containers in opposed two directions with separate driving sources.

SUMMARY OF THE INVENTION

An object of the present invention is to provide an analyzing apparatus which is capable of efficiently analyzing test solutions without the need for spending time to be required only for stirring operation, and an analyzing method thereof.

Another object of the present invention is to provide an analyzing apparatus in which light measurement can be performed on a test solution contained in one of containers while a test solution contained in another container is being stirred, and an analyzing method thereof.

Another object of the present invention is to provide an analyzing apparatus which enables the test solutions to be stirred in some of the containers during the conveyance of a train of containers, and an analyzing method thereof.

Another object of the present invention is to provide an analyzing apparatus in which the conveyance of a train of containers and stirring of the test solutions in the containers can be performed by using one driving device, and an analyzing method thereof.

In the present invention, a train of containers is provided on a movable holder, and the train is conveyed such that it passes through a container rotating area and a container non-rotating area. The motion of the movable holder driven by a driving source is transmitted to the containers located in the container rotating area as a rotational force of the containers on their own axes. In the container non-rotating area, a light beam of a photometer is formed so that the light measurement can be performed to measure the test solutions in the containers which arrived at the non-rotating area. The movable holder continuously moves the distance which is a plurality of times the distance between the adjacent containers, and both the stirring of the test solutions and the light measurement of the test solutions are performed during this movement. Precisely, each of the test solutions is measured by the photometer in a range of 2 to 10 seconds after it has stopped rotating on its own axis.

BRIEF DESCRIPTION OF THE DRAWINGS

FIG. 2 schematically shows the vicinity of a reaction table of the structure of FIG. 1;

FIG. 3 is a section view taken along the line III—III of FIG. 2;

FIG. 4 shows a reaction container employed in the embodiment shown in FIG. 1;

DETAILED DESCRIPTION OF THE PREFERRED EMBODIMENTS

Figure 1:
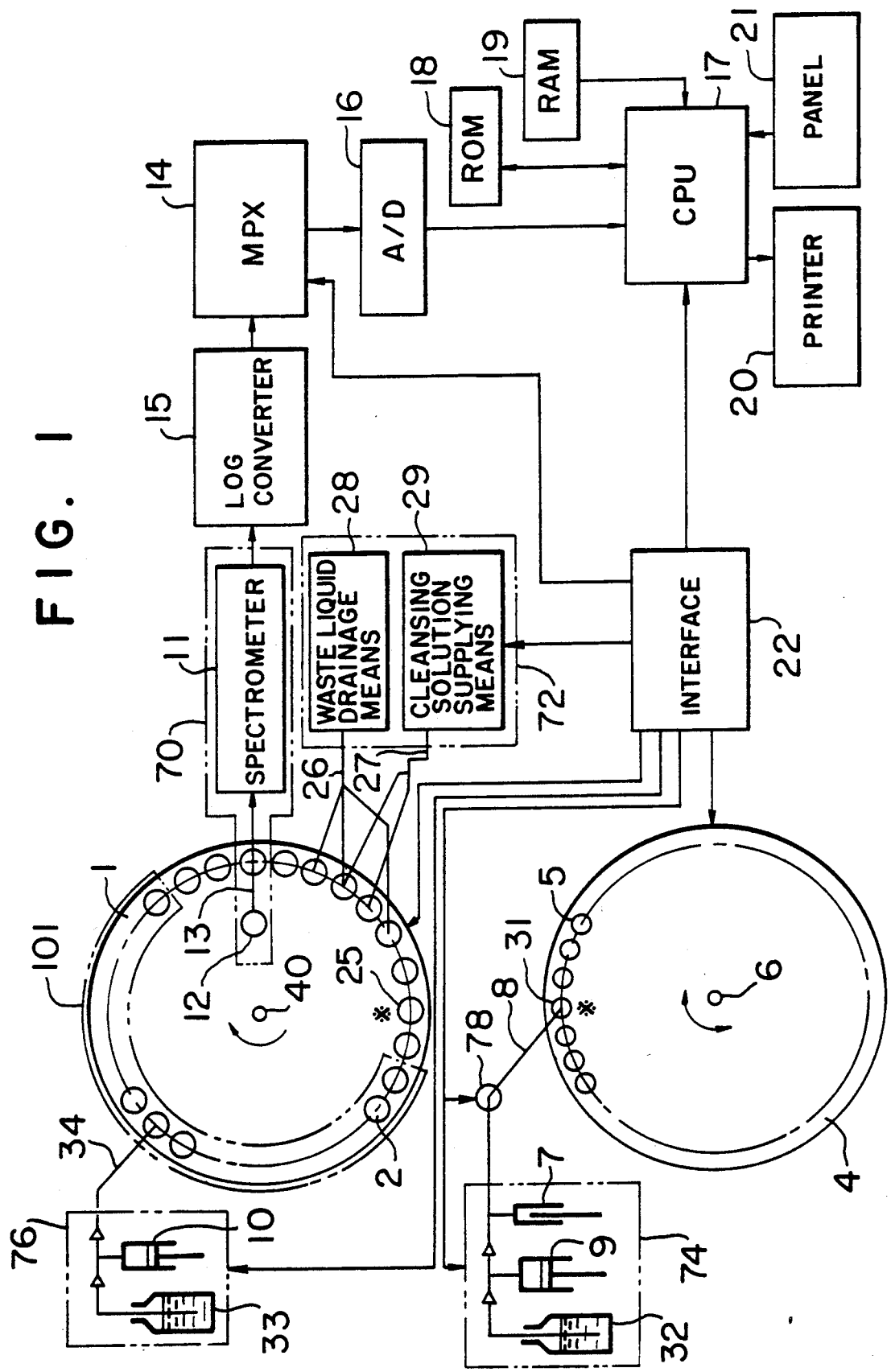
FIG. 1 is a schematic view of a blood sample analyzing apparatus, showing a first embodiment of the present invention.

In a preferred form of the present invention, an analyzing apparatus includes a motion transmitting means that can be made to contact the outer wall surfaces of reaction containers arranged on a reaction turntable. The motion transmitting means has a fixed contact member, and transmits the motion of the train of containers which are conveyed by the turntable as the rotational force of the reaction containers on the turntable on their own axes. As the reaction container rotates on its own axis, the liquid contained in that reaction container is stirred.

Note that the outer wall surface of the reaction container includes a surface of the wall that forms the reaction container, a surface of a strip provided on the outside of the reaction container to prevent sliding of the reaction container, and a surface of a container covering member which is formed integrally with the reaction container.

In one of the embodiments of the present, invention, a turntable has through holes along its periphery at fixed intervals. A cylindrical reaction container is held by the inner periphery of each of the holes. A bearing is provided in each of the holes so that the reaction container placed in the bearing can be smoothly rotated on its own axis. A friction member is provided concentrically with respect to the turntable at a position where it makes contact with the side of the reaction container. The coefficient of friction between the friction member and the containers is set to an appropriate value. The reaction containers are rotated on their own axes by means of friction caused when the turntable is rotated without the need for a special reaction container rotating device.

Further, rotation of the reaction containers on their own axes can be stopped at a particular location while the turntable is rotating by providing notches in the fixed friction member disposed in the circumferential direction. The friction member, which is called a "friction flange", or the surface thereof may be made of a relatively soft material having a high coefficient skin friction. For example, silicone rubber is suitable for the material. The friction member itself is generally made of a synthetic resin. In that case, if a sufficient amount of frictional force is not produced between the, reaction containers and the friction member, gear like irregularities are formed on the surface of the friction member to engage with irregularities formed on the reaction containers so as to allow a rotational force to be efficiently transmitted. The friction produced between the through-hole and each of the reaction containers held by the corresponding through-hole in the turntable is low. This prevents the reaction container from being moved while the turntable is being stopped. This also prevents the container from being shifted. The through-holes in the turntable are adequately, made of a synthetic resin having a lower coefficient of friction than that of silicone rubber, such as a polyethylene resin, a vinyl chloride resin or an ABS resin.

In the embodiment shown in FIG. 1, which is described later, a rotating state in which the turntable conveys the train of reaction containers and a stationary state in which the turntable does not convey the train of reaction containers are alternately repeated. As the conveying operation is stopped, the rotation of the reaction containers on their own axes stops due to the friction between the through-holes in the turntable and the reaction containers. However, after the rotation of the reaction containers has been stopped, inertia causes the liquid in the reaction containers to keep rotating for a while. If a friction member made of, silicone rubber is employed and if the turntable is stopped after it has made one revolution, the liquid in the reaction containers continues rotating for about 4 seconds after the rotation of the cylindrical reaction containers made of glass have stopped. The time the liquid in the reaction containers keeps rotating varies, depending on the shape of the reaction containers and the properties of the liquid. While the liquid is rotating alone, the sample and the reagent in the liquid can be stirred and mixed more uniformly.

During the rotation of the turntable, the reaction containers located on the turntable make contact with the friction member and are thereby rotated on their own axes. In other words, the two different objects, i.e., the positioning of the turntable and the rotation of the reaction containers, can be achieved by the provision of a driving device for the turntable. Further, the friction member, which is disposed in the circumferential direction in such a manner that it makes contact with the reaction containers, does not make contact with the reaction containers at a point where the rotation of the reaction containers is not required, such as at a point where light measurement is performed or at a point where the reaction containers are supplied to or removed from the turntable. The friction member may be brought into contact with the inner side or the outer side of the train of reaction containers arranged in a circular conveying path, or both of the inner and outer sides of the reaction containers.

FIG. 1 schematically shows an analyzing apparatus as an embodiment of this invention. Reaction turntable 1 can be rotated on a rotary shaft 40 in clockwise direction. A plurality of, e.g. forty, of cuvettes 2 are held on the periphery of reaction turntable 1. Sample turntable 4 can be rotated on a rotary shaft 6 in either the forward or backward direction. A plurality of sample cups 5, each containing a liquid sample such as, for example, blood serum, are held on the periphery of sample turntable 4.

The sampling operation is performed by a distributor 74, which has a sampling probe 8 and a probe shifter 78. The probe shifter 78 can horizontally shift the sampling probe 8 tipped with a nozzle, from intake position 31 to ejection position 25 and also vertically shift the probe 8 in both intake and ejection positions 31 and 25. Distributor 74 also has a microsyringe 7 for taking in the sample, a syringe 9 for supplying the sample and a first vessel 32 for liquid reagent.

A reagent supplier 76 has a length of pipe 34 extended to the train of cuvettes held by the reaction turntable 1, a syringe 10 for supplying reagent and a second vessel 33 for liquid reagent. The supply of reagent for the cuvettes in the reaction turntable 1 is performed by reagent supplier 76. The number of reagent supplies 76 to be used is equal to the number of the analysis items each of which requires two kinds of reagent for analysis.

A drive means for driving the reaction turntable 1 is connected through an interface 22 shown in FIG. 1, with a central processing unit (CPU) 17. CPU 17 causes motor 44 to stop when the number of detection signals delivered exceeds a predetermined number which is greater than the number of perforations on disc 45, for example, when forty-one detection signals are delivered. In this case, turntable 1 also makes more than one revolution.

The light measuring apparatus, photometer 70 in FIG. 1, has a lamp 12 as a light source and a spectrometer 11. Photometer 70 is shown in greater detail in FIG. 2. A light beam 13 travelling from light source 12 to spectrometer 11 traverses the path along which the train of cuvettes is conveyed. The beam guided into the spectrometer 11 is broken down into different wavelength components by means of a concave grating 58 and the respective components are detected by semiconductor photodetectors array 59 arranged in accordance with the wavelengths to be detected. Each of cuvette 2 supported on the turntable 1 and conveyed along a circular path is made to traverse the beam 13 in the photometer during its circular movement. Since beam 13 is made to pass through the cuvette 2 and the liquid contained therein, the total absorption of light, that is, the absorption by the cuvette 2 plus the absorption by the liquid therein, can be detected. The beam path is so positioned that when turntable 1 is stationary, the beam 13 passes through the center of the cuvette 2 which, for example, may be the thirtieth cuvette counted clockwise from ejection position 25. The respective photodetectors 59 are connected with corresponding logarithmic amplifiers 15, each of which is connected with two multiplexers 14. Each of the two multiplexers 14 extracts a photo-signal corresponding to a single wavelength. Two of the signals corresponding to the two wavelengths extracted by the two multiplexers are respectively digitalized by an A/D converter 16 and the digital signals are received by the CPU 17.

A waste liquid drainage pipe 26 and a cleaning solution supply pipe 27 are provided between the sample ejection position and the position of intersection between the light beam 13 and the path of the train of cuvettes. A cleaning apparatus 72 has a waste liquid drainage means 28 to which drainage pipe 26 is connected and a cleaning solution supplying means 29 to which supply pipe 27 is linked. The waste liquid drainage pipe 26 and cleaning solution supply pipe 27 are shifted down into the cuvettes located at a predetermined positions when turntable 1 is stopped. CPU 17 in FIG. 1 is connected through a bus line with the interface 22, A/D converter 16, a read-only memory (or ROM) 18, a random-access memory (or RAM) 19, a manipulation panel 21 and a printer 20.

When the sampling cup 5 containing a serum sample is sent to sampling position 31 on the sample turntable 4, the tip of the sampling probe 8 is immersed in the liquid in the sample cup 5 so that a quantity of serum is sucked up and held in the probe 8. The probe 8 is then shifted to ejection position 25 and the serum held in the probe 8 is ejected into the cuvette 2 resting at the ejection position 25 while the syringe 9 ejects the specified quantity of the first reaction reagent into the same cuvette.

The inner wall surfaces of cuvettes or reaction containers 2 are coated with a special antibody required for antigen-antibody reaction, for example, antiCEA antibody. A first reagent, which is a liquid containing enzyme-labeled antiCEA antibody, is accommodated in first reagent vessel 32. Immune reaction is started when the sample containing CEA and the first reagent are ejected into the reaction container located at ejection position 25, by which are immune complex starts to be formed on the inner wall surface of reaction container.

After the completion of the above sampling operation, the reaction table 1 starts rotating clockwise and rotates through 369 degrees which corresponds to the angle through which 41 cuvettes, that is, the cuvettes whose number is greater by one than that of all the cuvettes held on the turntable 1, pass through the ejection position 25.

After the above rotational operation, the cuvette 2 containing the apportioned sample and the first reaction reagent is located at the position in advance by one pitch, i.e., 9 degrees, clockwise of the ejection position 25. During one revolution of turntable 1, all the cuvettes 2 on turntable 1 traverse light beam 13. Accordingly, when each cuvette 2 crosses the beam 13, the spectrometer 11 performs absorbance measurement. The output of spectrometer 11 is sent through the logarithmic amplifier 15 to the multiplexer 14, which selects the signal having a desired wavelength. The output of multiplexer 14 is sent through the A/D converter 16 to the CPU 17 for storage in the RAM 19. The above series of operation is repeated every thirty seconds, provided that a cycle consisting of the time for which turntable 1 is moving and the time for which it is stationary, is set equal to 30 sec. As the cycles advance, a particular sample advances, pitch by pitch, clockwise.

A tube 34 for adding the second reagent to the sample is located at the fifteenth cuvette counted clockwise from ejection position 25. Accordingly, any particular sample initially resting at the ejection position 25 and undergoing the first reaction there, will receive the second reagent to initiate the second reaction in the fifteenth cycle.

The preceding operations are effected through the control of the respective mechanisms by the CPU 17 via the interface 22 in accordance with the program stored in ROM 18. The operation panel 21 is used to supply measurement conditions and to start and stop measurement. The results of the measurement of analysis items are calculated using data obtained after the second reaction has been started, the obtained results being printed out by a printer 20.

In the embodiment shown in FIG. 1, the path in which the train of reaction containers 2 is conveyed consists of a container rotating area in which the reaction containers are rotated on their own axes and a container non-rotating area in which the rotational force is not transmitted to the reaction containers. The container rotating area 101 extends over more than half of the total number of the reaction containers on the reaction turntable 1. An area other than the container rotating area represents the non-rotating area. A curved friction flange 120 is fixedly provided in the container rotating area 101, as shown in FIG. 2.

FIG. 2 is a plan view, with part broken away, of the vicinity of the reaction turntable 1 of the apparatus of FIG. 1. Note that the reaction containers 2 are shown in FIG. 2 in a number less than that shown in FIG. 1 in order to simplify the explanation.

Annular bearings 171 are provided in the 40 holes formed in the reaction turntable 1. The friction produced between each of the bearings 171 and the reaction container is low. The reaction turntable 1 has an upper plate 1a and a lower plate 1b. The inner diameter of each of the bearings 171 provided in the upper plate 1a is made substantially equal to the outer diameter of the reaction container 2. The lower plate 1b has a plurality of concave portions 52 formed at positions corresponding to the holes formed in the upper plate 1a. The spherical bottom portions of the containers 2 are received by the concave portion 52. In this way, a shift of the containers 2 is prevented and the containers can be rotated on their own axes in the concave portion 52 when a relatively strong force is exerted on the outer walls of the containers 2.

The train of reaction containers is alternately moved in a conveyance state and stopped in a stationary state by the pulse motor 44 mounted on a base 50. The friction flange 120 made of silicone rubber is disposed around the train of reaction containers. The inner peripheral surface of the friction flange 120 makes contact with the outer walls of all the reaction containers located within the container rotating area 101.

A strip of plastic 115 is fixed on part of the outer surface of each of the reaction containers 2 made of glass, as shown in FIG. 4. This strip of plastic 115 is formed with a gear like shaped portion over a surface thereof so as to allow the container conveying force to be surely transmitted to the reaction container as the rotational force thereof through the friction flange 120. If the reaction container 2 is made of a plastic, the strip 115 is formed integrally with the reaction container 2. The reaction container 2 also has a plurality of vane-like shaped fins 116 formed on the inner surface of the bottom portion thereof. These fins 116 allow the liquid contained in the reaction container to be efficiently stirred as the reaction container is rotated on its own axis. The beam of light 13 passes through the reaction container set in the analyzing apparatus at a position below the strip of plastic 115.

It is preferable for the inner peripheral surface of the friction flange 120 to be formed with a gear like portion over a surface thereof so that the portion can be engaged with the gear like shapped portion formed on the strip 115 of the container 2. In that case, it is not required that the friction flange may be made from a material having a high coefficient of friction and the flange may be made of a generally employed plastic.

Since the friction produced between the friction flange 120 and the reaction container 2 is higher than the friction caused between the reaction container and the bearing 171, the rotation of the reaction turntable 1 causes the reaction containers located within the rotating area 101 to be rotated on their own axes in the direction indicated by an arrow 60.

A disk 45 mounted on the lower portion of the rotary shaft 40 of the reaction turntable 1 is a spur gear. The driving force of the stepping motor 44 is transmitted to the disk 45 through a transmitting gear 56. The friction flange 120 is fixed to a vertical portion 51 of the base 50 by a fixture 109.

In the non-rotating area where no friction flange 120 is disposed, the reaction containers 2 on the reaction turntable 1 are not rotated in the bearings 171. On the other hand, since the reaction containers 2 on the reaction turntable 1 are kept in contact with the friction flange 120 between a rotation starting position 117 and a rotation ending position 118 while the reaction turntable 1 is moved clockwise, they keep rotating on their own axes in this area. After they have passed the rotation ending position 118, they no longer contact with the friction flange 120 and, therefore, the rotation of the containers is stopped. However, the liquid contained in the reaction containers keeps rotating for a while by means of inertia.

The rotation of the liquid contained in the reaction container 2 must be substantially stopped during the measurement of the liquid by the light beam 13. A stable measured value can be obtained only when the motion of the liquid in the container 1 completely stops while the container 2 is being conveyed from the rotation ending position 118 to the light measured position 119 in FIG. 1.

After the rotation of the reaction container has stopped, the light measuring operation is started only when the rotation of the liquid in the reaction container is substantially stopped. On the other hand, it is essential to process as many specimens as possible within a predetermined time. The time between the ending of the rotation of the reaction container and the starting of light measurement is set at 4 to 5 seconds, if the employed serum sample is a normal reaction liquid. In the case when the viscosity of the reaction liquid is high, this time can be shortened, because the inertia readily stops the motion of the reaction liquid. However, at least 2 seconds are required before the light measurement is started. Even if the rotational speed of the reaction container is high, for example, even if it is 1000 rpm, the reaction liquid, which continues rotating due to inertia after the rotation of the container has been stopped, stops within 7 seconds. In consequence, the distance or the angle between the rotation ending position 118 and the light measured position 119 in FIG. 2 is so set that it ensures 7 seconds between the starting of the light measurement and the ending of the rotation of the container on its own axis. This time interval is set to 10 seconds at a maximum.

Figure 5:
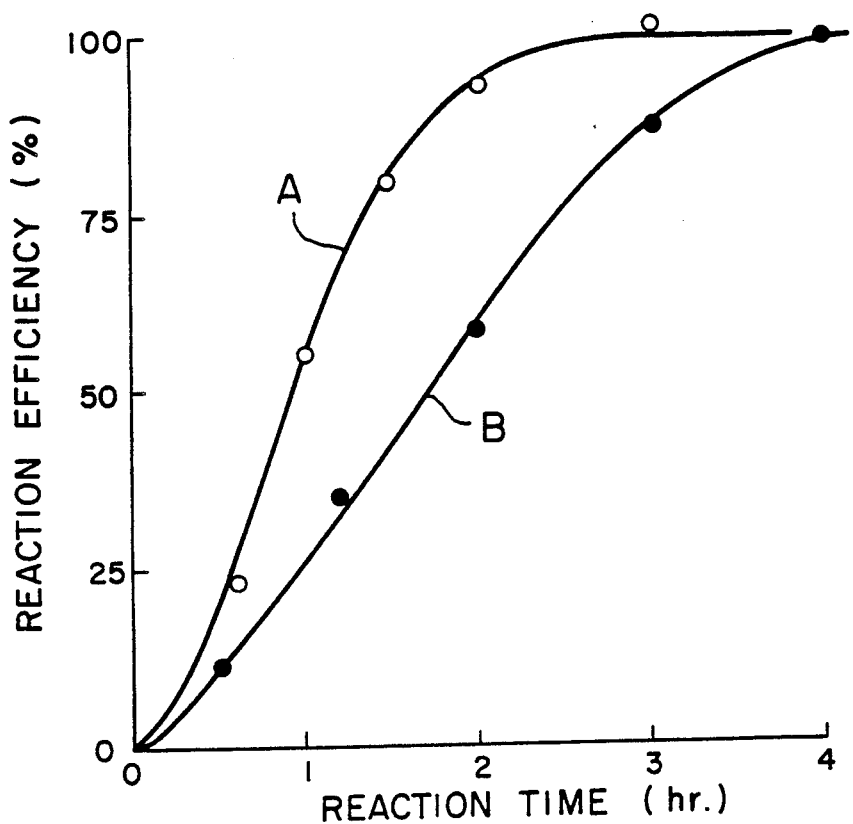
FIG. 5 is a graph showing the experiment results obtained on the efficiency of stirring operation.

FIG. 5 shows the results of the experiments which were conducted to show the effect of stirring in the analysis performed by using the analyzing apparatus shown in FIG. 1. In the experiments, the effect of stirring to the rate of antigen-antibody reaction in the measurement of cartinoembryonic antigen (hereinafter referred to as CEA), was examined. The CEA is micro-protein contained in blood, and was measured by enzyme immunoassay method (hereinafter referred to as EIA method). When a specimen containing CEA and enzyme labeled-antiCEA antibody (hereinafter referred to as enzyme labeled-antibody) are ejected into a reaction container in the inner wall of which is coated with antiCEA antibody, CEA complex (antiCEA antibody - CEA - enzyme-labeled antibody) is formed on the inner wall of the reaction container.

The rate of antigen-antibody reaction itself is very high. However, since the concentration of CEA is blood is extremely low, for example, it is contained in an amount which is several nanomol to several tens nanomol per milliliter, if the reaction container containing the specimen and the reagent is left stationary so that the CEA complex is formed only by thermodynamic diffusion, reaction occurs at a very slow rate. However, if the CEA in the solution is caused to collide forcibly against the wall surface of the reaction container by stirring the solution so as to raise the probability of reaction, the rate of reaction rises.

In the experiments, the antigen-antibody reactions were performed under two different conditions, i.e., in one case, the reaction container was left stationary while the antigen-antibody reaction was occurring, and in the other case, the solution in the container was stirred in accordance with the present invention. In both cases, the reaction efficiency was obtained at various reaction times. After the antigen-antibody reaction, the contents of the container were treated in the same way in both cases. More specifically, free enzyme-labeled antibody which was not bonded to the antigen was first removed by cleansing. Thereafter, stroma and a coloring agent were ejected into the reaction container which was cleansed and on which the immune complex remained so as to color the stroma and the coloring agent by the enzyme contained in the enzyme-labeled antibody bonded to the antigen, and the degree of coloring was measured using the spectrophotometer. As is clear from FIG. 5, in the stationary state B, it took about 4 hours to complete the reaction, whereas in the stirring state A which conforms to the present invention, the reaction was completed in about 2 hours, and the rate of reaction doubled.

Figure 6:
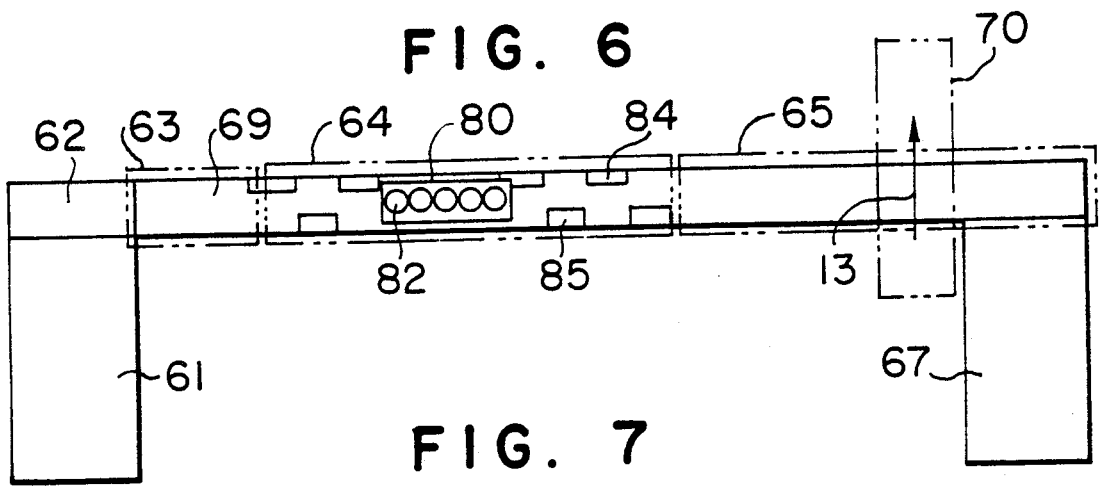
FIG. 6 is a schematic view of an analyzing apparatus, showing a second embodiment of the present invention.

Another embodiment of the present invention will be described below with reference to FIGS. 6 and 7. In this automatic blood analyzing apparatus, a plurality of reaction containers held on a rack are conveyed in a straight line along a conveying path. The transparent reaction containers are respectively held in a plurality of holes formed in the rack 80. Since the friction between each of the reaction containers and the rack is small, when the container makes contact with a contact member, the motion of the rack which conveys the reaction containers is transmitted to the container and the container therefore rotates on its own axis.

The rack 80 is supplied from a rack supplying portion 61 to a sample adding position 62 located on a conveying path 69, where blood serum sample is ejected into each of reaction containers 82 held on the rack 80 while the rack 80 is at stop. The rack 80 is then conveyed to a reagent adding position 63, where reagent solution corresponding to the analysis item is ejected into each of the reaction containers 82 while the rack 80 is at stop. Subsequently, the rack 80 is continuously conveyed on the conveying path 69 through a container rotating area 64 and a non-rotating area 65. During the conveyance of this rack 80, the reaction liquid contained in each of the reaction containers 82 traverses the light beam 13, and light measurement of the reaction liquid is performed. The rack 80 is then retrieved into a rack retrieving portion 67.

While the reaction containers held on the rack 80 pass through the container rotating area 64, they are rotated on the rack 80 on their own axes so as to allow the liquids contained in the reaction containers to be stirred. A pair of contact plates 84 and 85 are fixedly provided along the conveying path 69 in the container rotating area 64. The contact plates 84 and 85 respectively consist of a plurality of contact ends 86, 87, 88, 91, 92, 93 which protrude so that they make contact with the outer walls of the containers.

Figure 7:
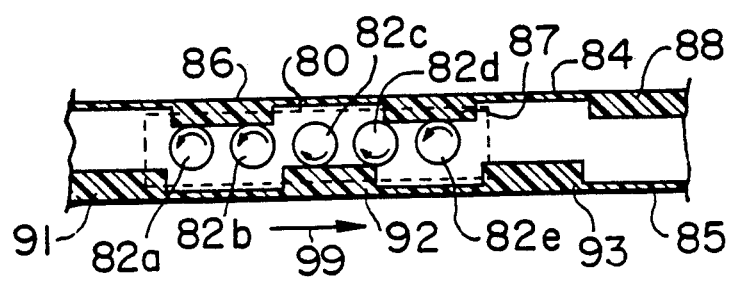
FIG. 7 shows how the containers located in a container-rotating area rotate on their own axes in the embodiment shown in FIG. 6.

In the container rotating area 64, when the rack 80 is conveyed by a driving device (not shown) in the direction indicated by an arrow 99, as shown in FIG. 7, the reaction containers on the rack 80 are successively brought into contact with the large number of contact ends. At this time, the motion of the rack is transmitted to the reaction containers on the rack 80 by means of friction, and the reaction containers are thereby rotated on their own axes. Since the contact ends 86 to 88 of the contact plate 84 and the contact ends 91 to 93 of the contact plate 85 are alternately located on the different sides of the conveying path, the reaction containers are alternately rotated in opposite directions, i.e., clockwise and counterclockwise. In the state shown in FIG. 7, reaction containers 82a and 82b which are in contact with the contact end 86 are rotating counterclockwise, reaction containers 82c and 82d which are in contact with the contact end 92 are rotating clockwise, and a reaction container 82e which is in contact with the contact end 87 is rotating counterclockwise. In this way, the liquid contained in each of the reaction containers can be stirred efficiently.

Once the train of reaction containers enters the non-rotating area 65, the rotation of the reaction containers on their own axis stops. The rotational motion of the reaction liquid contained in the reaction containers caused by the inertia also stops before the reaction container reaches the light beam 13.

What is claimed is:

1. An apparatus for analyzing the contents of a plurality of containers, each of said containers having an axis of rotation and an outer periphery, comprising:
    means for holding said plurality of containers for accommodating a liquid to be stirred therein about said axis of rotation;
    fixed container rotating and non-rotating areas;
    drive means for driving said means for holding to move said plurality of containers through said container rotating and non-rotating areas;
    transmitting means for transmitting motion of said means for holding caused by said drive means to a rotational force acting on said containers, said transmitting means including fixed flange means in said container rotating area for frictionally engaging said plurality of containers to cause each of said containers to rotate on its said axis in said container rotating area; and
    a photometer for irradiating each of said plurality of containers with a light beam in said non-rotating area.

2. An analyzing apparatus according to claim 1, wherein said containers are made of a transparent material, and the outer periphery of each of said containers has irregularities that engage said flange means.

3. An analyzing apparatus according to claim 1, wherein said drive means is a pulse motor for driving said means for holding intermittently.

4. An analyzing apparatus according to claim 1, wherein said flange means engages a plurality of said containers simultaneously.

5. An analyzing apparatus according to claim 1, wherein said flange means has a plurality of surfaces that engage said containers, and wherein said surfaces are alternately disposed on opposite sides of said containers.

6. An analyzing apparatus according to claim 1, further comprising means for controlling said photometer for beginning an irradiating of said containers ten seconds after movement of said containers stops.

7. An analyzing apparatus according to claim 1, further comprising means for controlling said photometer for beginning an irradiating of said containers within two seconds after movement of said containers stops.

8. An analyzing apparatus according to claim 1, wherein said containers have vein shaped fins on an interior portion thereof for stirring.

9. An analyzing apparatus according to claim 2, wherein said containers have vein shaped fins on an interior portion thereof for stirring.

10. An analyzing apparatus according to claim 1, wherein said drive means drives said plurality of containers in only one direction.

11. An analyzing apparatus according to claim 10, wherein said drive means is a pulse motor that intermittently drives said holding means.

12. An analyzing apparatus according to claim 1, wherein said holding means holds said plurality of containers in alignment and said drive means drives said holding means to move said plurality of containers along a circular path.

13. An analyzing apparatus according to claim 1, wherein said holding means holds said plurality of containers in alignment and said drive means drives said holding means to move said plurality of containers along a straight path having opposite sides.

14. An analyzing apparatus according to claim 12, wherein said fixed flange means is arcuate and has a face engaging said plurality of containers along a portion of said circular path.

15. An analyzing apparatus according to claim 14, wherein said flange means is positioned outside said circular path and extends for greater than one-half of said circular path.

16. An analyzing apparatus according to claim 13, wherein said fixed flange means is positioned to engage said containers along one of the sides of the straight path.

17. An analyzing apparatus according to claim 13, wherein said fixed flange means is positioned to alternately engage said containers on both sides of said straight path so that said containers rotate in opposite directions.

18. An analyzing apparatus according to claim 1, wherein said holding means is driven in rotation by said drive means to move said containers in a circular path, and wherein said fixed flange means is an arcuate flange positioned to engage said containers along a portion of said circular path.

19. An analyzing apparatus according to claim 18, wherein said holding means comprises upper and lower discs, said upper disc having through holes with bearings for receiving said containers therein, and said bottom disc having concave portions aligned with said through holes for supporting a bottom portion of said containers.

20. An analyzing apparatus according to claim 18, wherein said flange is positioned outside said circular path.

21. An apparatus for analyzing the contents of a plurality of containers, each container having an outer periphery, comprising:
   means for holding a plurality of containers, each of said containers accommodating a liquid therein to be stirred about an axis of rotation of said containers;
   means for driving said means for holding to move said containers in a path through fixed rotating and non-rotating areas;
   fixed flange means in said container rotating area for frictionally engaging said containers, said holding means supporting said containers for rotation about said container axes, and said driving means being further for driving said containers into engagement with said fixed flange means to rotate said containers about said axes, respectively; and
   means for irradiating each of said containers in said non-rotating area.

22. An analyzing apparatus according to claim 21, wherein said holding means holds said containers in a circular array, and wherein said fixed flange means is an arcuate flange positioned to engage said containers as said containers move through said container rotating area.

23. A method for analyzing a plurality of containers, each having an axis of rotation, comprising the steps of:
   holding said plurality of containers for accommodating a liquid to be stirred therein about said axis of rotation;
   driving said plurality of containers through fixed container rotating and non-rotating areas;
   transmitting motion of said plurality of containers caused by said driving to a rotational force acting on said containers by driving said containers into engagement with a fixed flange in said container rotating area to cause each of said containers to rotate on its own said axis in said container rotating area; and
   irradiating each of said plurality of containers with a light beam in said non-rotating area.

24. An analyzing apparatus according to claim 23, further comprising the step of ejecting at least one of a sample and a reagent into a container located at a predetermined position while the conveyance of said containers is stopped.

* * * * *